US00PP36768P2

(12) United States Plant Patent
Guerrero

(10) Patent No.: US PP36,768 P2
(45) Date of Patent: Jun. 24, 2025

(54) ***GYPSOPHILA* PLANT NAMED 'ESM G057'**

(50) Latin Name: *Gypsophila hybrida*
Varietal Denomination: ESM G057

(71) Applicant: GENVIV HOLDINGS, LLC, Miami, FL (US)

(72) Inventor: Maria Elena Guerrero, Quito (EC)

(73) Assignee: GENVIV HOLDING, LLC, Miami, FL (US)

( * ) Notice: Subject to any disclaimer, the term of this patent is extended or adjusted under 35 U.S.C. 154(b) by 0 days.

(21) Appl. No.: 18/981,531

(22) Filed: Dec. 14, 2024

(51) Int. Cl.
*A01H 5/02* (2018.01)
*A01H 6/30* (2018.01)

(52) U.S. Cl.
USPC ..... Plt./354

(58) Field of Classification Search
USPC ..... Plt./354
CPC ..... A01H 5/02; A01H 5/00; A01H 6/30
See application file for complete search history.

(56) References Cited

U.S. PATENT DOCUMENTS

PP19,479 P2 * 11/2008 Hooijman ..... A01H 6/30
Plt./354

* cited by examiner

*Primary Examiner* — June Hwu
(74) *Attorney, Agent, or Firm* — C. Anne Whealy

(57) ABSTRACT

A new and distinct cultivar of *Gypsophila* plant named 'ESM G057', characterized by its strong flowering stems; uniform and freely flowering habit; large and dense inflorescences with large double white-colored flowers; relatively high cut flower yield; and good postproduction longevity.

1 Drawing Sheet

Botanical designation: *Gypsophila hybrida.*
Cultivar denomination: 'ESM G057'.

CROSS-REFERENCED TO CLOSELY-RELATED APPLICATIONS

A U.S. Plant Patent application for the *Gypsophila* Plant Named 'ESM G052' was filed by the Inventor, Maria Elena Guerrero concurrently with the instant application on Dec. 14, 2024.

A European Community Plant Breeder's Rights application for the instant plant was filed by the Applicant/Assignee, Genviv Holdings, LLC of Miami, Florida on Sep. 29, 2023, application number 2023/2060 and published on Dec. 15, 2023. Foreign priority is not claimed to this application.

A Colombia Plant Breeder's Rights application for the instant plant was filed by the Applicant/Assignee, Genviv Holdings, LLC of Miami, Florida on Nov. 18, 2024, application number A243196. Foreign priority is not claimed to this application.

BACKGROUND OF THE INVENTION

The present invention relates to a new and distinct cultivar of *Gypsophila* plant, botanically known as *Gypsophila hybrida*, grown commercially as a cut flower, and hereinafter referred to by the name 'ESM G057'.

The new *Gypsophila* plant is a product of a planned breeding program conducted by the Inventor in El Quinche, Pichincha, Ecuador. The objective of the breeding program is to create new productive and uniform *Gypsophila* plants with numerous large double flowers and good postproduction longevity.

The new *Gypsophila* plant originated from a cross-pollination conducted by the Inventor in El Quinche, Pichincha, Ecuador in November 2010 of a proprietary selection of *Gypsophila hybrida* identified as line 251, not patented, as the female, or seed, parent with a proprietary selection of *Gypsophila hybrida* identified as line 210, not patented, as the male, or pollen, parent. The new *Gypsophila* plant was discovered and selected by the Inventor as a single flowering plant from within the progeny of the stated cross-pollination in a controlled environment in El Quinche, Pichincha, Ecuador in March 2016.

Asexual reproduction of the new *Gypsophila* plant by cuttings in a controlled environment in El Quinche, Pichincha, Ecuador since June 2017 has shown that the unique features of this new *Gypsophila* plant are stable and reproduced true to type in successive generations.

SUMMARY OF THE INVENTION

Plants of the new *Gypsophila* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'ESM G057'. These characteristics in combination distinguish 'ESM G057' as a new and distinct *Gypsophila* plant:

1. Strong flowering stems.
2. Uniform and freely flowering habit.
3. Large and dense inflorescences with large double white-colored flowers.
4. Relatively high cut flower yield.

5. Good postproduction longevity.

In side-by-side comparisons, plants of the new *Gypsophila* differ from plants of the female parent selection in the following characteristics:

1. Plants of the new *Gypsophila* have denser inflorescences than plants of the female parent selection.
2. Flowers of plants of the new *Gypsophila* are double-types whereas flowers of plants of the female parent selection are semi-double-types.
3. Flowers of plants of the new *Gypsophila* have more petals and petaloids than flowers of plants of the female parent selection.

In side-by-side comparisons, plants of the new *Gypsophila* differ from plants of the male parent selection in the following characteristics:

1. Plants of the new *Gypsophila* are more vigorous and denser than plants of the male parent selection.
2. Stems and flowering stems of plants of the new *Gypsophila* are sturdier than and not as flexible as stems and flowering stems of the male parent selection.
3. Plants of the new *Gypsophila* flower about four to six weeks earlier than plants of the male parent selection.
4. Flowers of plants of the new *Gypsophila* are double-types whereas flowers of plants of the male parent selection are semi-double-types.

Plants of the new *Gypsophila* can also be compared to plants of *Gypsophila hybrida* 'Esm Alicia', disclosed in U.S. Plant Pat. No. 19,479. In side-by-side comparisons, plants of the new *Gypsophila* differ from plants of 'Esm Alicia' in the following characteristics:

1. Plants of the new *Gypsophila* flower two weeks later than plants of 'Esm Alicia'.
2. Flowers of plants of the new *Gypsophila* are double-types whereas flowers of plants of 'Esm Alicia' are semi-double-types.
3. Flowers of plants of the new *Gypsophila* have more petals and petaloids than flowers of plants of 'Esm Alicia'.

Plants of the new *Gypsophila* can also be compared to plants of *Gypsophila hybrida* 'ESM G052', disclosed in a U.S. Plant patent application Ser. No. 18/981,530 filed concurrently. In side-by-side comparisons, plants of the new *Gypsophila* differ from plants of 'ESM G052' in the following characteristics:

1. Plants of the new *Gypsophila* are not as vigorous as plants of 'ESM G052'.
2. Plants of the new *Gypsophila* flower about one week earlier than plants of 'ESM G052'.
3. Inflorescences of plants of the new *Gypsophila* have more flowers than inflorescences of plants of 'ESM G052'.
4. Flowers of plants of the new *Gypsophila* have more petals/petaloids than flowers of plants of 'ESM G052'.
5. Plants of the new *Gypsophila* yield more flowering stems per plant as plants of 'ESM G052'.

BRIEF DESCRIPTION OF THE PHOTOGRAPH

The accompanying photograph illustrates the overall appearance of the new *Gypsophila* plant showing the colors as true as it is reasonably possible to obtain in colored reproductions of this type. Colors in the photograph may differ slightly from the color values cited in the detailed botanical description which accurately describe the colors of the new *Gypsophila* plant.

The photograph is composed of a side perspective view of a typical flowering stem of 'ESM G057' (upper left); close-up view of a typical inflorescence of 'ESM G057' (lower left); close-up view of a typical flower of 'ESM G057' (upper right); and close-up view of upper and lower surfaces of typical leaves of 'ESM G057' (center right).

DETAILED BOTANICAL DESCRIPTION

The aforementioned photograph and following observations and measurements describe plants grown in ground beds in an outdoor nursery in El Quinche, Pichincha, Ecuador in March and under cultural practices which approximate those generally used in commercial cut *Gypsophila* production. During the production of the plants, day temperatures ranged from 14° C. to 21° C., night temperatures ranged from 6° C. to 9° C. and light levels averaged 19.3 klux. Plants were pinched one time three weeks after planting and were 16 weeks old when the photographs and the detailed description were taken. In the following description, color references are made to The Royal Horticultural Society Colour Chart, Sixth Edition, 2015, except where general terms of ordinary dictionary significance are used.

Botanical classification: *Gypsophila hybrida* 'ESM G057'.

Commercial classification: Cut flower *Gypsophila*.

Parentage:

*Female, or seed, parent*.—Proprietary selection of *Gypsophila hybrida* identified as line 251, not patented.

*Male, or pollen, parent*.—Proprietary selection of *Gypsophila hybrida* identified as line 210, not patented.

Propagation:

*Type*.—By vegetative cuttings.

*Time to initiate roots, summer*.—About 15 days at temperatures ranging from 8° C. to 38° C.

*Time to initiate roots, winter*.—About 15 days at temperatures ranging from 14° C. to 28° C.

*Time to produce a rooted young plant, summer*.—About five to six weeks at temperatures ranging from 8° C. to 38° C.

*Time to produce a rooted young plant, winter*.—About five to six weeks at temperatures ranging from 14° C. to 28° C.

*Root description*.—Medium to fine in thickness, fibrous; typically close to 161A in color; actual color of the roots is dependent on substrate composition, water quality, fertilizer, substrate temperature and age of roots.

*Rooting habit*.—Moderately freely branching; dense.

Plant description:

*Appearance*.—Perennial cut flower; erect and strong flowering stems; inverted triangle form; uniform and freely flowering habit; large double white-colored flowers; moderately vigorous growth habit and moderate growth rate.

*Branching habit*.—About six primary branches each with about five to eight secondary branches developing; relatively high cut flower yield, about 9.4 flowering stems are typically harvested per year.

*Plant height*.—About 117 cm.

*Plant diameter or spread*.—About 56 cm.

*Flowering stems*.—Length: About 105.7 cm. Diameter: About 3.9 mm. Internode length: About 6.6 cm. Strength: Strong. Texture and luster: Smooth, glabrous; matte. Color, developing: Close to 146B.

Color, developed: Close to 146B; at the internodes, close to 146C tinged with close to N187A.

Leaf description:

*Arrangement*.—Opposite, decussate, simple; sessile.

*Length*.—About 7.5 cm.

*Width*.—About 1.5 cm.

*Shape*.—Lanceolate.

*Apex*.—Acute.

*Base*.—Cuneate.

*Margin*.—Entire.

*Texture and luster, upper and lower surfaces*.—Smooth, glabrous; matte.

*Venation pattern*.—Parallel.

*Color*.—Developing leaves, upper and lower surfaces: Close to NN137B. Fully expanded leaves, upper surface: Close to 139B; venation, close to NN137B. Fully expanded leaves, lower surface: Close to NN137C and 139C; venation, close to NN137B.

Flower description:

*Flower arrangement and habit*.—Symmetrical and uniform compound cymes with numerous white-colored flowers, flowers symmetrical, rotate and double; freely flowering habit, about 586 flowers per inflorescence; flowers face mostly upright.

*Flowering response*.—In Ecuador, plants flower year round; early flowering habit; plants begin flowering about 14 weeks after planting.

*Post-production longevity*.—As a cut flower, flowers last for about 13 days; on the plant, flowers last for about 35 days; flowers persistent.

*Fragrance*.—Slightly fragrant; pleasant.

*Inflorescence height*.—About 64.4 cm.

*Inflorescence diameter*.—About 39.3 cm.

*Flower diameter*.—About 1 cm.

*Flower depth* (*height*).—About 6 mm.

*Flower buds*.—Length: About 2.6 mm. Diameter: About 2.4 mm. Shape: Nearly globose. Texture and luster: Smooth, glabrous; matte. Color: Close to 146A tinged with close to N199A.

*Petals*.—Quantity per flower: About 89 petals/petaloids in about four to five whorls and fused at the base in clusters. Length: About 5.1 mm. Width: About 1.9 mm. Shape: Spatulate. Apex: Truncate to emarginate. Margin: Entire; slightly undulate. Texture and luster, upper and lower surfaces: Smooth, glabrous; waxy; matte. Color: When opening and fully opening, upper surface: Close to NN155D; venation, close to NN155D; color becoming closer to 155B with subsequent development. When opening and fully opening, lower surface: Close to NN155D; venation, close to NN155D; color becoming closer to 155B with subsequent development.

*Petaloids* (*transformed stamens*).—Length: About 4.6 mm. Width: About 1.6 mm. Shape: Variable, roughly spatulate or linear. Apex: Truncate or emarginate. Margin: Entire; moderately undulate. Texture and luster, upper and lower surfaces: Smooth, glabrous; matte. Color: When opening and fully opening, upper surface: Close to NN155D; venation, close to NN155D; color becoming closer to 155B with subsequent development. When opening and fully opening, lower surface: Close to NN155D; venation, close to NN155D; color becoming closer to 155B with subsequent development.

*Sepals*.—Quantity per flower: About five to seven fused at the base to form a cupped star-shaped calyx. Length: About 3.7 mm. Width: About 2.6 mm. Shape: Lanceolate. Apex: Acute. Margin: Entire. Texture and luster, upper and lower surfaces: Smooth, glabrous; matte. Color: When developing, upper and lower surfaces: Close to NN137B. Fully developed, upper and lower surfaces: Close to 136B.

*Peduncles*.—Length: About 7 mm. Diameter: About 1.1 mm. Strength: Strong. Angle: About 37.8° from lateral branch axis. Texture and luster: Smooth, glabrous; matte. Color: Close to 146B.

*Pedicels*.—Length: About 8.4 mm. Diameter: About 2.2 mm. Strength: Moderately strong. Angle: About 41.6° from peduncle axis Texture and luster: Smooth, glabrous; matte. Color: Close to NN137B tinged with close to N199A.

*Reproductive organs*.—Stamens: Quantity per flower: If present, about four to seven. Filament length: About 4.4 mm. Filament color: Close to NN155D. Anther shape: Reniform to globose. Anther length: About 0.7 mm. Anther color: Close to 162D. Pollen amount: None observed. Pistils: Quantity per flower: One. Pistil length: About 5 mm. Style length: About 3.9 mm. Style color: Close to NN155D. Stigma shape: Curved apiculate. Stigma diameter: About 0.4 mm to 0.7 mm. Stigma color: Close to NN155D. Ovary color: Close to 144A. Seeds and fruits: To date, seed and fruit production has not been observed on plants of the new *Gypsophila*.

Pathogen & pest resistance: To date, plants of the new *Gypsophila* have not been observed to be resistant to pathogens and pests common to *Gypsophila* plants.

Temperature tolerance: Flowering plants of the new *Gypsophila* have been observed to tolerate temperatures ranging from about 6° C. to about 28° C.

It is claimed:

1. A new and distinct *Gypsophila* plant named 'ESM G057' as herein illustrated and described.

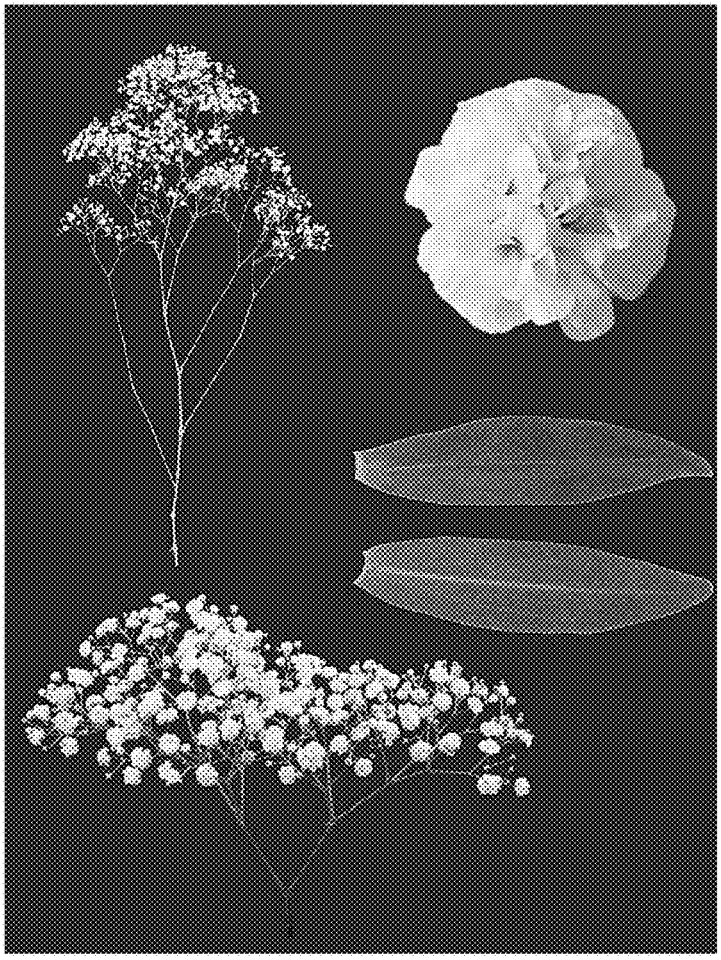

* * * * *